United States Patent [19]
Swezey et al.

[11] Patent Number: 5,948,013
[45] Date of Patent: Sep. 7, 1999

[54] SELF-INFLATING BACK PILLOW AND COLD THERAPY DEVICE

[76] Inventors: Robert L. Swezey, 10532 Garwood Pl., Los Angeles, Calif. 90024; Richard Swezey, 148 N. Wilton Pl., Los Angeles, Calif. 90004

[21] Appl. No.: 08/893,014

[22] Filed: Jul. 15, 1997

Related U.S. Application Data

[60] Provisional application No. 60/021,810, Jul. 16, 1996.

[51] Int. Cl.$^6$ ....................................................... A61F 7/00
[52] U.S. Cl. ................... 607/108; 607/112; 5/636
[58] Field of Search ..................... 607/108, 112, 607/114, 104; 5/636, 641, 490, 492

[56] References Cited

U.S. PATENT DOCUMENTS

| | | |
|---|---|---|
| 3,864,766 | 2/1975 | Prete, Jr. . |
| 3,872,525 | 3/1975 | Lea et al. . |
| 4,518,200 | 5/1985 | Armstrong . |
| 4,702,235 | 10/1987 | Hong . |
| 5,168,590 | 12/1992 | O'Sullivan ................... 5/490 |
| 5,179,942 | 1/1993 | Drulias et al. . |
| 5,195,948 | 3/1993 | Hill et al. .................... 602/19 |
| 5,271,114 | 12/1993 | Kjersem ...................... 5/640 |
| 5,437,618 | 8/1995 | Sikes ......................... 602/19 |
| 5,458,628 | 10/1995 | Cipolla ...................... 607/112 |
| 5,727,266 | 3/1998 | Pang .......................... 5/490 |

*Primary Examiner*—Brian L. Casler
*Assistant Examiner*—Ryan Carter
*Attorney, Agent, or Firm*—J. E. McTaggart

[57] ABSTRACT

A therapeutic pillow, that can be fastened to the backrest of a variety of chairs and seats, provides air-pressure-assisted lower back support that can be conveniently adjusted by the user for optimum level of support. The self-inflating pillow, utilizing an interacting combination of two types of expanded compressible core material stuffing and air pressure, never requires an external pump, compressor or lung/breath inflation. The front surface of the pillow provides a hook-and loop type attachment surface for versatile attachment of support straps for securing the pillow in place to the chair, and also provides for versatile attachment of thermal packets, e.g. for cold therapy. The pillow can be folded or rolled in a deflated carrying mode.

13 Claims, 2 Drawing Sheets

SELF-INFLATING BACK PILLOW AND COLD THERAPY DEVICE

Benefit is claimed under 35 U.S.C, § 119(e) of pending provisional application #60/021,810 filed Jul. 16, 1996.

FIELD OF THE INVENTION

The present invention relates to the field of therapeutic devices, and more particularly it relates to a back-support pillow that provides a user-adjustable degree of back support without requiring any pump or other external apparatus.

BACKGROUND OF THE INVENTION

Back support in a seated position is important to all persons, particularly those prone to back problems. Since traditional pillows are made with a fixed resilient structure, finding lower back support of desired firmness and thickness often entails locating and trying several different pillows or combinations before a suitable one is found. Bed support structures such as coil spring mattresses and water bed technology have not been found adaptable to pillows.

Ordinary pillows of known art are most commonly made resilient through the use of an appropriate stuffing material such as down, cellular foam or the like. As an alternative, running a distant second, air can be used for resilience in a sealed pillow bag, typically inflated by compressed air from an external source such as human breath, a motorized compressor or a hand operated pump, e.g. a bicycle tire pump. When the air pillow is inflated to a desired degree, the pressure source is removed and a valve seals the enclosure and prevents air escape as long as the enclosure remains air tight.

Unfortunately the air pillow is inherently subject to loss of air through leakage over time, and thus the more stable and reliable stuffed pillow has heavily predominated.

The air pillow does offer a significant advantage over the stuffed pillow in that it can be adjusted to a desired degree of effective thickness and support by controlling the amount of contained air. Once inflated to a working degree of support, the support is easily reduced by releasing air; however to increase the support again requires additional air input from one of the above-mentioned external pressurizing sources. This inherent inconvenience has greatly limited the use of air pillows as adjustable back support devices. Inflatable flotation devices for water sport and air mattresses for camping are popular because they can be deflated, folded and stored in a small space.

An example of a specialized institutional application that benefits from the adjustable feature of air inflation is found in hospital bed mattresses with multiple independently inflatable cells for preventing bedsores.

A further consideration in an adjustable back support pillow is the desirability of facilities for retaining thermo/therapeutic devices, e.g. cold packs for alleviating back pain.

DISCUSSION OF RELATED KNOWN ART

U.S. Pat. No. 5,195,948 to Hill et al discloses a therapeutic belt to be worn around the waist to act as an adjustable back support device. An air bladder is inflated by a manual pump.

U.S. Pat. No. 5,179,942 to Drulias discloses a lumbar support therapeutic heat/cooling/air pillow belt, including an elastic tensioning band portion of the belt encircling the user's waist, and a pocket for a thermal packet.

In U.S. Pat. No. 5,168,590, Sullivan discloses a therapeutic pillow cover having compartments for receiving hot/cold packs and/or pillow insert supports.

In U.S. Pat. No. 3,872,525, Lea et al disclose an inflatable pad having cellular foam encased in and bonded to an impervious envelope inflatable through a dual fine/coarse valve system utilizing two nested coaxial stopper plugs; a combination of resilient foam and fluid pressure from contained water or air.

U.S. Pat. No. 4,518,200 to Armstrong discloses a seat pad with adjustable lumbar support implemented by an inflatable bladder, inflated from an external hand-squeezed pump.

OBJECTS OF THE INVENTION

It is a primary object of the present invention to provide a lower back support pillow that is user-adjustable with regard to the degree of support.

It is a further object that the support pillow should be fully usable and adjustable without ever requiring any external source of fluid pressure such as a pump or the like.

It is a still further object that the support pillow of this invention provide convenient and versatile means for attachment of one or more thermal packets such as cooling devices for therapy and pain reduction.

SUMMARY OF THE INVENTION

The above-mentioned objects have been accomplished by the present invention of a pillow having a composite core with a main layer made from a firm resilient material and an auxiliary smaller core layer made from a vented core bag containing compliant stuffing material such as fiber and/or down. The two layers are enclosed in an airtight resilient main bag which is fitted with a valve having a rotary knob by which the user can seal or unseal the main bag for adjusting the amount of support.

The front side of the outer surface of the main bag is made to have a fastening surface, such as Velcro engagable loop, also known as "hook-and-loop", for engaging a pair of attachment straps for attachment around a chair backrest. The device is highly adaptable to chairs, seats, and other furniture such as folding chairs, auto seats, secretarial chairs, bus seats, sporting events seats, etc.

Furthermore, the fastening surface provides the option of attaching one or more thermal packets, typically cold packs, at any selected location(s).

While seated and utilizing the pillow, the user can easily adjust the degree of back support by manipulating the valve knob.

BRIEF DESCRIPTION OF THE DRAWINGS

The above and further objects, features and advantages of the present invention will be more fully understood from the following description taken with the accompanying drawings in which.

DETAILED DESCRIPTION

Figures 1, 2:
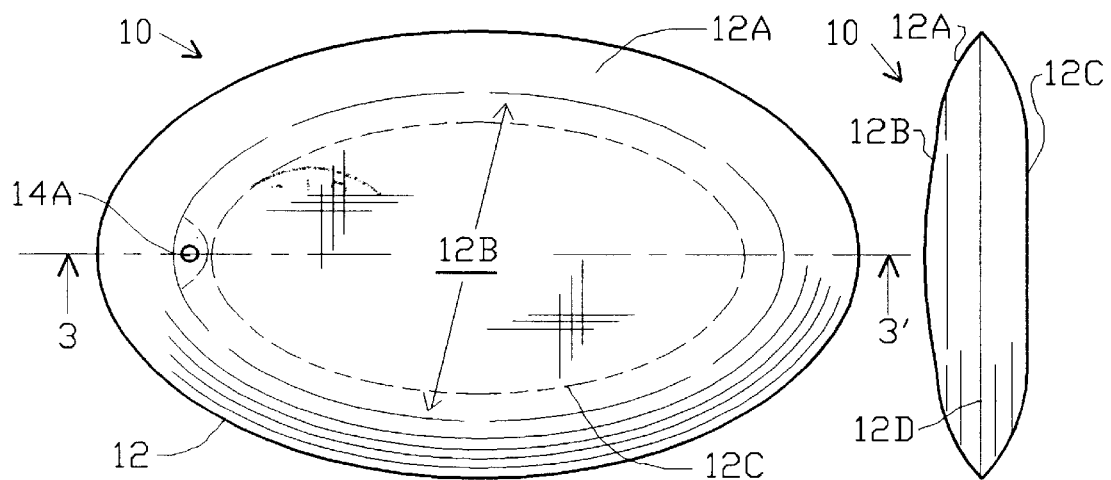
FIG. 1 is a front elevational view showing the outline of a therapeutic back support pillow according to the present invention.
FIG. 2 is a right hand side elevational view of the pillow of FIG. 1.

FIG. 1, a front elevational view of a therapeutic back support pillow 10 according to the present invention, shows the front panel 12A of main pillow bag 12 of an illustrative embodiment having an oval-shaped outline; a typical size would be 18" wide by 7" high. The front panel 12A of main bag 12 is made to provide a fastening surface 12B of a fabric fastening system such as Velcro engagable loop type which is available in polyester with a polyurethane film backing. The fastening material of surface 12B is adhesively attached to the main bag 12 or otherwise made integral therewith. Fastening surface 12B, which is made to extend over at least a major portion of the front panel 12A as shown, is intended to be pleasing to the touch or to sit against as well as providing fastening capability.

A knob 14A near the left side, i.e. the user's right side, operates a valve that allows the user to seal/unseal the main bag 12, which is made airtight.

In FIG. 2, a right hand side elevational view of pillow 10 of FIG. 1, the fastening surface 12B extends over the major portion of front panel 12A, which is seen to be made with a convex curvature while the main portion of rear panel 12C is made generally flat. Front panel 12A and rear panel 12C may be made from plastic material such as polyester, and may be joined to form an airtight peripheral seam 12D by a radio frequency process.

Figure 3:
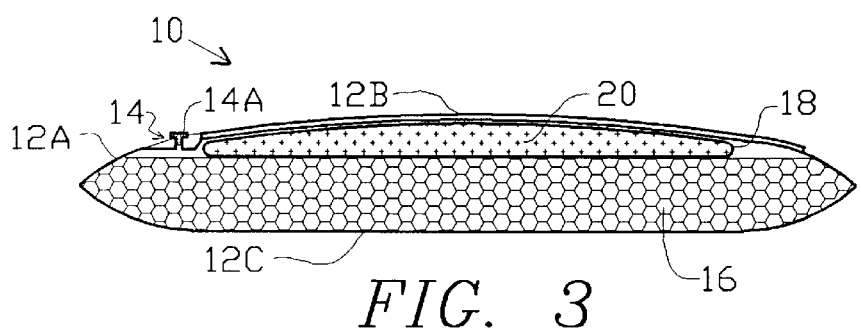
FIG. 3 is a cross-section taken through axis 3–3' of the pillow of FIG. 1.

FIG. 3, a cross-section of pillow 10 taken through axis 3–3' of FIG. 1, shows the main panels 12A and 12C enclosing two core layers: a main layer formed by foam core 16 and a secondary layer formed by an auxiliary bag 18 containing stuffing material 20 such as fiber or down, or mix thereof. Bag 18 is made non-airtight, i.e. able to "breathe", by fabricating it from woven fabric material, or by providing air vent holes if it is made from plastic such as polyvinyl. Bag 18 is preferably fastened against main core 16 by an adhesive. The main core 16 can be made from an open cell foam material, e.g. 1.8 lb, 34 I.F.D. open cell polyurethane.

A valve 14 for inflating/deflating bag 12 via knob 14A is seen near the left end of the front panel 12A, located in a slightly recessed region; alternatively valve 14 could be located elsewhere, e.g. at the outer perimeter of bag 12, on rear panel 12C or in a non-recessed region near an end of front panel 12A.

Figure 4:
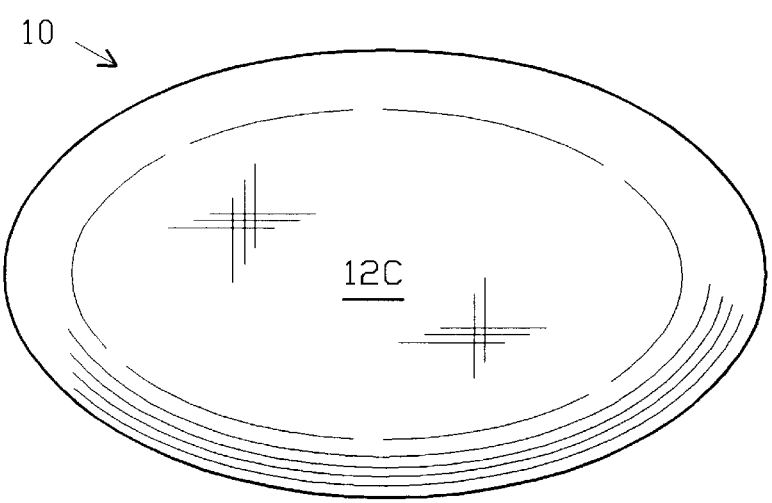
FIG. 4 is a rear elevational view of the pillow of FIGS. 1–3.

FIG. 4, a rear elevational view of pillow 10, showing the rear panel 12C. Typical dimensions for pillow 10 are 18" by 7" by 1¾".

Figure 5:
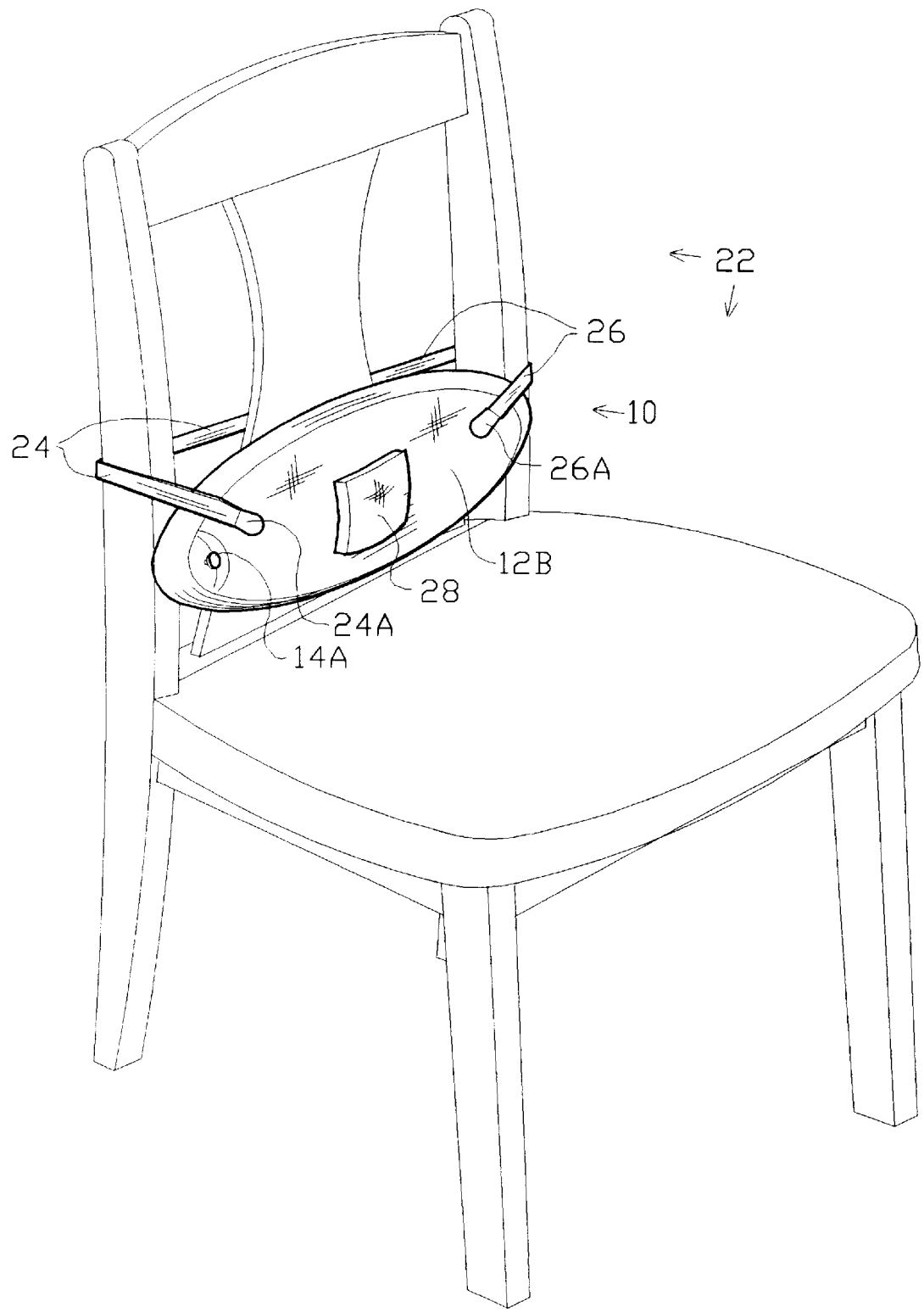
FIG. 5 is a three dimensional view of the pillow of FIGS. 1–4 attached in place against the backrest of a chair.

FIG. 5 is three-dimensional view of a therapeutic pillow 10 of the present invention shown attached to the backrest of a chair 22. A pair of attachment straps 24 and 26 have one end fastened to pillow 10 by attachment pads 24A and 26A which are made with attachment surfaces that matingly engage the front panel attachment surface 12B. Valve knob 14A is seen near the left hand end. An optional thermal packet 28, typically containing a cold gel or powder, and made available in various sizes and/or variable in size, is shown attached to surface 12B in a central region where it is held in place by a mating attachment surface on the rear of packet 28. Straps 24 and 26 are made to mate together at the rear of chair 22 by means of overlapping engagable loop portions by which the length can be set so as to hold pillow 10 in place.

To practice the present invention, initially, with no external pressure applied to pillow 10, knob 14A is rotated to open the valve and allow air to enter the main bag 12 until it self-inflates due to expansion of the resilient core layers 16 and 20 (FIG. 3) to their maximum uncompressed thickness. Then the valve is closed via knob 14A, capturing the air enclosed in bag 12; now the pressure of the captured air, adding to the resilient pressure of the core materials, holds the pillow 10 at a maximum thickness, ready to provide a maximum level of back support. Pillow 10 is then attached to a chair with straps 24 and 26 as described above and the user is seated against pillow 10 which initially provides maximum support as pressure from the user's back compresses pillow 10 and increases the air pressure in bag 12.

To reduce and adjust the level of support, air is released by operating knob 12A to open the valve momentarily so as to adjust the support to a desired level.

To increase the level of support, the user leans slightly forward to remove pressure from pillow 10 and opens the valve with knob 12A, allowing bag 12 to re-inflate, taking in air as required until a desired support level is attained and captured by closing the valve.

Optimally, the user perceives the sensation of a firm, friendly hand supporting the back.

The available range of support level can be set anywhere between the initial maximum level, as described above, and a minimum level that can be attained by opening the valve, squeezing pillow 10 so as to deflate it as much as possible, and then closing the valve so that core layers 16 and 20 are held in a compressed condition by a partial vacuum in bag 12, i.e. air pressure below atmospheric.

As an alternative to the oval outline shape of pillow 10 shown in FIGS. 1, 4 and 5, it can be made rectangular or any other desired practical shape. Furthermore the overall size and/or three-dimensional shape can be altered to provide a particular pattern of back support.

The invention can be practiced with alternative core configurations and materials selected to attain particular levels and patterns of firmness and support. As an alternative to the two-core layer structure in the embodiment disclosed above, auxiliary layer 20 can be eliminated, leaving only a monolithic layer 16, typically of open cell foam. Alternatively there can be three or more layers.

Valve knob 14A can be made dial-like or star-shaped, and may be molded of pliant, easy-to-grip material that allows fine tuning of the degree of firmness and support.

As an alternative to providing attachment surface 12A integral with main bag 12, surface 12A can be provided as part of a separate outer cover, enclosing main bag 12, optionally made removable for laundering and/or replacement.

As an alternative to, or in addition to provision for fastening straps 22 and 24 together by engagable loop means as indicated above, they can be made to fasten by buckle or snap-on means. Furthermore, the buckles could be weighted so that the straps could be directed over the top of the backrest of chair 22 with the buckles hanging downwardly behind the chair counterbalancing pillow 10, thus allowing maximum freedom to position pillow 10 optimally with respect to the user's back.

As a further alternative, the straps 22 and 24 can be easily removed if it is desired to utilize pillow 10 in the unfastened mode of a conventional pillow.

Straps 24 and 26 can also be constructed and arranged to secure the device for carrying in a deflated and folded mode.

The attachment arrangement, unique to this device, allowing the straps 24 and 26 or other items such as cold pack 28 to be attached anywhere on the pillow surface, also permit the pillow 10 to worn by the user like a belt for ambulatory back support.

The invention can be practiced with alternative core materials selected to provide a desired pressure distribution, degree of support and range of adjustment.

The invention may be embodied and practiced in other specific forms without departing from the spirit and essential characteristics thereof. The present embodiments are therefore to be considered in all respects as illustrative and not restrictive, the scope of the invention being indicated by the appended claims rather than by the foregoing description; and all variations, substitutions and changes which come within the meaning and range of equivalency of the claims are therefore intended to be embraced therein.

What is claimed is:

1. A self-inflating pillow, for back support of a human user seated on a seating device, comprising:
   a main bag made from airtight material, configured and arranged to form a shape that is generally flat on a rear side of the main bag and generally convex on a front side thereof;
   a primary stuffing pad of compressible expanded open-cell material contained within said main bag, disposed internally against the rear side thereof and constituting a primary core layer;
   a non-airtight convex-lens-shaped auxiliary secondary bag, smaller than said main bag, disposed within said main bag and affixed to said primary stuffing pad in a central region thereof forward of said primary stuffing pad;
   a secondary stuffing pad of particulate material, contained within said secondary bag, constituting a secondary core layer that, while resilient, tends to conform to body shape; and
   an air valve, installed in a selected region of said main bag, made and arranged to enable the user to manually select either of two operating states: a closed state wherein the bag and the air valve form an airtight enclosure, and an open state wherein air can freely flow through the valve;
   whereby the user is enabled to vary the pillow in thickness within a range between a full natural expansion and a total compression of said primary stuffing pad and said secondary stuffing pad, as follows: (a) to decrease the thickness the valve is opened, pressure is applied externally so as to compress the pillow to a desired decreased thickness while exhausting a quantity of air from the pillow, then the valve is closed, thus retaining the desired thickness, and (b) to increase the thickness, the valve is opened, a quantity of air is allowed to enter the pillow, as the stuffing pads expand to the desired thickness, then the valve is closed, thus retaining the desired increased thickness.

2. The self-inflating pillow as defined in claim 1 further comprising:
   a pair of fastening straps made from elastic webbing and arranged to removably attach said pillow to a back rest portion of the seating device;
   attachment means for removably attaching a first end of each of said fastening straps to said pillow; and
   strap joining means for removably attaching a second end of each of said fastening straps to each other.

3. The self-inflating pillow as defined in claim 2 wherein:
   said attachment means for removably attaching a first end of said straps to said pillow comprises engagable loop fabric affixed to said pillow, including two appropriate attachment locations thereof, and engagable hook fabric affixed to each of said fastening straps in a region near the first end thereof; and
   said strap joining means comprises an area of engable hook fabric affixed to a first one of said attachment straps near the second end thereof, and an area of engagable loop fabric affixed to a second one of said attachment straps near the second end thereof;
   said removable straps, said engagable hook fabric and said engagable loop fabric being structured and arranged to fasten said pillow to a back region of the seating device.

4. The self-inflating pillow as defined in claim 3 further comprising an outer cover made from fabric material and having at least a major portion of one side made to expose a surface of engagable loop fabric.

5. The self-inflating pillow as defined in claim 4 wherein at least one of said pair of fastening straps is configured to have a short length of non-elastic webbing material at the second end thereof, so as to provide a finger grip region for attachment to and detachment from the other strap.

6. The self-inflating pillow as defined in claim 5 wherein said pair of fastening straps is configured to each have a tab of resilient material molded onto the non-elastic webbing material at the second end thereof, so as to provide a thickened finger grip region for attachment to and detachment from the other strap.

7. The self-inflating pillow as defined in claim 5 wherein said pair of fastening straps is configured to each have a short length of non-elastic webbing material and a molded resilient tab at the first end thereof, so as to facilitate attachment to and detachment from said pillow.

8. The self-inflating pillow as defined in claim 1 further comprising a thermal packet configured and arranged to attach removable to said pillow in a central region thereof.

9. The self-inflating pillow as defined in claim 4 further comprising;
   an area of engagable loop fabric affixed on a front side of said pillow in a central region thereof; and
   a thermal packet having a region of engagable hook material configured and arranged to provide mating removable attachment to said region of engagable loop fabric on the front side of said pillow.

10. The self-inflating pillow as defined in claim 4 wherein said primary stuffing pad is made from open cell polyurethane foam.

11. The self-inflating pillow as defined in claim 4 wherein said secondary stuffing pad is made from organic down material.

12. A self-inflating pillow, for back support of a human user seated on a seating device, comprising:
   a main bag made from airtight material, configured and arranged to form a shape that is generally flat on a rear side of the main bag and generally convex on a front side thereof;
   a primary stuffing pad of compressible expanded open-cell material contained within said main bag, disposed against the rear side thereof and constituting a primary core layer;
   a non-airtight convex-lens-shaped auxiliary bag, smaller than said main bag, disposed within said main bag and affixed to said primary stuffing pad in a central region thereof;
   a secondary stuffing pad of particulate material, contained within said auxiliary bag, constituting a secondary core layer that, while resilient, tends to conform to body shape;
   an outer cover made from fabric material made to expose an exterior surface of engagable loop fabric;
   a pair of fastening straps made from elastic webbing and made to have:

at a first end thereof length of non-elastic webbing providing a surface region of engagable hook fabric material made arranged to removably engage the surface of engagable loop fabric of said cover of said pillow, at a second end of a first of said fastening straps, a region of non-elastic webbing providing a surface region of engagable hook fabric;

at a second end of a second of said fastening straps, a region of non-elastic webbing providing a surface region of engagable loop fabric made and arranged to removably engage said region hook fabric of the first fastening strap, whereby said pillow can be removably fastened to a back region of said seating device; and an air valve, installed in a selected region of said main bag, made and arranged to enable the user to manually select either of two operating states: a closed state wherein the bag and the air valve form an airtight enclosure, and an open state wherein air can freely flow through the valve;

whereby the user is enabled to vary the pillow in thickness within a range between a full natural expansion of the primary and secondary stuffing pads and a full compression thereof as follows: (a) to decrease the thickness the valve is opened, pressure is applied externally so as to compress the pillow to a desired decreased thickness while exhausting a quantity of air from the pillow, then the valve is closed, thus retaining the desired thickness, and (b) to increase the thickness, the valve is opened, a quantity of air is allowed to enter the pillow, as the stuffing pads expand to the desired thickness, then the valve is closed, thus retaining the desired increased thickness.

13. The self-inflating pillow as defined in claim 12 further comprising a thermal packet having a region of engagable hook material configured and arranged to provide mating removable attachment to engagable loop material on the front side of said pillow.

* * * * *